US012686656B2

(12) United States Patent
Shinmen et al.

(10) Patent No.: US 12,686,656 B2
(45) Date of Patent: Jul. 21, 2026

(54) ALKYLAMINE COMPOSITION AND METHOD FOR STORING SAID ALKYLAMINE COMPOSITION

(71) Applicant: CENTRAL GLASS COMPANY, LIMITED, Ube (JP)

(72) Inventors: Masutaka Shinmen, Ube (JP); Kenta Watanabe, Ube (JP); Azusa Miyake, Ube (JP)

(73) Assignee: CENTRAL GLASS COMPANY, LIMITED, Yamaguchi (JP)

( * ) Notice: Subject to any disclaimer, the term of this patent is extended or adjusted under 35 U.S.C. 154(b) by 792 days.

(21) Appl. No.: 18/010,559

(22) PCT Filed: Jun. 23, 2021

(86) PCT No.: PCT/JP2021/023740
§ 371 (c)(1),
(2) Date: Dec. 15, 2022

(87) PCT Pub. No.: WO2022/004516
PCT Pub. Date: Jan. 6, 2022

(65) Prior Publication Data

US 2023/0257339 A1 Aug. 17, 2023

(30) Foreign Application Priority Data

Jul. 3, 2020 (JP) ................................ 2020-115757

(51) Int. Cl.
*C07C 209/84* (2006.01)
*C07C 209/90* (2006.01)
*C07C 211/07* (2006.01)

(52) U.S. Cl.
CPC .......... *C07C 209/84* (2013.01); *C07C 209/90* (2013.01); *C07C 211/07* (2013.01)

(58) Field of Classification Search
CPC .... C07C 209/84; C07C 211/07; C07C 209/90
See application file for complete search history.

(56) References Cited

U.S. PATENT DOCUMENTS

| | | | |
|---|---|---|---|
| 5,840,987 | A | 11/1998 | Tsuji |
| 2005/0000790 | A1 | 1/2005 | Beck et al. |
| 2006/0016526 | A1 | 1/2006 | Mizutani et al. |
| 2011/0166387 | A1 | 7/2011 | Ruppin et al. |
| 2021/0331085 | A1 | 10/2021 | Shinmen et al. |

FOREIGN PATENT DOCUMENTS

| | | |
|---|---|---|
| CN | 101289548 | 10/2008 |
| CN | 101648874 | 2/2010 |
| CN | 101955431 | 1/2011 |
| CN | 104262165 A * | 1/2015 |
| CN | 110526849 | 12/2019 |
| CN | 110590634 | 12/2019 |
| CN | 111004129 | 4/2020 |
| CN | 111004130 | 4/2020 |
| CN | 111018719 | 4/2020 |

(Continued)

OTHER PUBLICATIONS

The Sigma-Aldrich product catalogues (2019)("Sigma") (Year: 2019).*
T. Wilkins, Metano Tote Talk Blog (2017) ("Wilkens") (Year: 2017).*
English translation of Decision of Refusal issued Sep. 2, 2025 in corresponding Japanese Patent Application No. 2022-533912.
Chemical substances: n-butylamine, Anzen site of workplace, Jan. 16, 2018.
Farumashia, vol. 38, No. 4, pp. 301-303, 2002.
Various metal containers, Chem-Station, Oct. 7, 2019.
Amines, Toyo Petrochemical Industries, Ltd., Dec. 9, 2017, cited in Decision of Refusal.

(Continued)

*Primary Examiner* — Alexander R Pagano
*Assistant Examiner* — Frank S. Hou
(74) *Attorney, Agent, or Firm* — Wenderoth, Lind & Ponack, L.L.P.

(57) ABSTRACT

The alkylamine composition of the present disclosure contains: an alkylamine represented by the following formula (1) in an amount of 99.5% by volume or more; and water in an amount of 10 ppm by mass or more and 100 ppm by mass or less:

[Chem. 1]

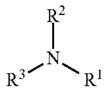

(1)

wherein N is a nitrogen atom; $R^1$ is a C1-C10 hydrocarbon group optionally having a ring, a heteroatom, or a halogen atom; $R^2$ and $R^3$ are each independently a hydrogen atom or a C1-C10 hydrocarbon group optionally having a ring, a heteroatom, or a halogen atom; provided that the hydrocarbon group, when it has a carbon number of 3 or more, may have a branched chain structure or a ring structure and that the heteroatom in the hydrocarbon group is a nitrogen atom, an oxygen atom, a sulfur atom, or a phosphorus atom; further, $R^1$ and $R^2$, when both of them are hydrocarbon groups having a carbon number of 1 or more, may be directly bonded to each other to form a ring structure; further, $R^1$ or $R^2$, which is directly bonded by a double bond to form a ring structure, may form an aromatic ring in the absence of $R^3$; $R^1$, $R^2$, and $R^3$ may be hydrocarbon groups which are the same as or different from one another; and $R^1$ has at least one hydrogen atom at α carbon bonded to the nitrogen atom.

10 Claims, No Drawings

(56) References Cited

FOREIGN PATENT DOCUMENTS

| | | | | |
|---|---|---|---|---|
| CN | 111072495 | | | 4/2020 |
| JP | 50-059305 | | | 5/1975 |
| JP | S5059305 | A | * | 5/1975 |
| JP | 62-48671 | | | 3/1987 |
| JP | 3-287566 | | | 12/1991 |
| JP | 07-173119 | | | 7/1995 |
| JP | 09-202737 | | | 8/1997 |
| JP | 10-139738 | | | 5/1998 |
| JP | 2002-105064 | | | 4/2002 |
| JP | 2003-081885 | | | 3/2003 |
| JP | 2011-526611 | | | 10/2011 |
| JP | 2012-106935 | | | 6/2012 |
| JP | 2014-214152 | | | 11/2014 |
| JP | 2019-524746 | | | 9/2019 |
| JP | 6813788 | | | 1/2021 |
| WO | 2004/060900 | | | 7/2004 |
| WO | 2018/017830 | | | 1/2018 |

OTHER PUBLICATIONS

International Search Report issued Aug. 10, 2021 in International Application No. PCT/JP2021/023740.

Office Action issued Nov. 16, 2024 in corresponding Chinese Patent Application No. 202180040150.3, with machine translation.

"Handbook of Organics and Chemicals", published by Chemical Industry Press (1985), pp. 494-496.

"N-Butyl Isocyanate Synthesis Process Modification", River North Chemical, vol. 31, No. 9 (2008), pp. 51-52.

Zhang et al., "Continuous Synthesis of Butylamine from Chlorobutane", Lake South Chemical, vol. 30, No. 4 (2000), pp. 27-29.

Author unknown, "Major degradation mechanism of nitrogen-containing functional groups in drugs" Disassembly of scientific literature, pp. 1-5, https://mp.weixin.qq.com/s/Md1dM5YbVzJoRFsvBhelwQ, Jan. 2, 2020, concise explanation in reference CB (see D13).

Office Action issued Mar. 25, 2026, in corresponding Chinese Patent Application No. 202180040150.3, with English language translation.

* cited by examiner

ALKYLAMINE COMPOSITION AND METHOD FOR STORING SAID ALKYLAMINE COMPOSITION

TECHNICAL FIELD

The present disclosure relates to an alkylamine composition and a method for storing the alkylamine composition.

BACKGROUND ART

Alkylamines, including n-butylamine, are used in the production process of pharmaceutical products and the production process of semiconductors. The purity of raw materials used in such production processes of pharmaceutical products and semiconductors is preferably as high as possible.

Alkylamines however often suffer discoloration or a decline in purity during storage. As a method for preventing such discoloration during storage, Patent Literature 1 discloses a method including adding hydrazine to an aromatic amine for stabilization, thereby preventing discoloration.

CITATION LIST

Patent Literature

Patent Literature 1: JP H03-287566 A

SUMMARY OF INVENTION

Technical Problem

The method disclosed in Patent Literature 1 includes addition of an additive containing hydrazine to a compound to be stored. In such a case, the amine composition contains the additive itself or a substance derived from the additive. Use of the amine composition in the production process of pharmaceutical products and the like may possibly cause production of a product that does not meet the required properties.

In view of the above issue, the present disclosure aims to provide an alkylamine composition that contains a small amount of an ingredient which is unlikely to have an adverse effect in the production process of pharmaceutical products and the like, that has excellent storage stability, and that is unlikely to suffer an increase in impurities even after long-term storage. The present disclosure also aims to provide a method for stably storing the alkylamine composition.

Solution to Problem

The present inventors made intensive studies to find that the formation of imines during long-term storage of alkylamines causes a decline in purity, and that in alkylamine compositions containing a small amount of water, a decline in purity due to the formation of imines during long-term storage can be reduced and the total amount of impurities, including water, can also be reduced. Thus, the present disclosure was completed.

Specifically, an alkylamine composition of the present disclosure contains: an alkylamine represented by the following formula (1) in an amount of 99.5% by volume or more; and water in an amount of 10 ppm by mass or more and 100 ppm by mass or less:

[Chem. 1]

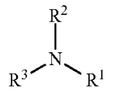

(1)

wherein N is a nitrogen atom; $R^1$ is a C1-C10 hydrocarbon group optionally having a ring, a heteroatom, or a halogen atom; $R^2$ and $R^3$ are each independently a hydrogen atom or a C1-C10 hydrocarbon group optionally having a ring, a heteroatom, or a halogen atom; provided that the hydrocarbon group, when it has a carbon number of 3 or more, may have a branched chain structure or a ring structure and that the heteroatom in the hydrocarbon group is a nitrogen atom, an oxygen atom, a sulfur atom, or a phosphorus atom; further, $R^1$ and $R^2$, when both of them are hydrocarbon groups having a carbon number of 1 or more, may be directly bonded to each other to form a ring structure; further, $R^1$ or $R^2$, which is directly bonded by a double bond to form a ring structure, may form an aromatic ring in the absence of $R^3$; $R^1$, $R^2$, and $R^3$ may be hydrocarbon groups which are the same as or different from one another; and $R^1$ has at least one hydrogen atom at $\alpha$ carbon bonded to the nitrogen atom.

Since the alkylamine composition of the present disclosure contains water in an amount of 10 ppm by mass or more and 100 ppm by mass or less, the formation of an imine, which is an impurity, can be inhibited over a long period of time. The alkylamine composition contains water in an amount of 10 ppm by mass or more and 100 ppm by mass or less. When the alkylamine composition is used in the production process of pharmaceutical products and the like, such a very small amount of water in the alkylamine composition is unlikely to cause production of a product that does not meet the required properties. On the other hand, the water in the composition can inhibit the formation of an imine which may possibly cause production of a product that does not meet the required properties. Even when water is considered a potentially problematic impurity, the total amount of impurities including water is small, allowing the composition to be suitable for use in pharmaceutical products and the like.

When the alkylamine composition contains water in an amount of less than 10 ppm by mass, the formation of an imine is hardly inhibited, which increases the imine content of the composition. Use of such a composition in the production process of pharmaceutical products and the like may possibly affect the properties of the resulting product. When the alkylamine composition contains water in an amount of more than 100 ppm by mass, the imine content of the composition can be made small but the water itself may affect the properties of the product when the composition is used as a raw material in the production of pharmaceutical products and the like.

In the alkylamine composition of the present disclosure, the alkylamine is preferably n-butylamine.

When the alkylamine in the alkylamine composition is n-butylamine, the alkylamine composition can be used as a raw material for producing pharmaceutical products or as an optimal compound for producing semiconductor devices.

The alkylamine composition of the present disclosure may further contain oxygen in an amount of 1 ppm by volume or more and 1000 ppm by volume or less.

The alkylamine composition of the present disclosure contains water within the above range, regardless of oxygen further contained in an amount of 1 ppm by volume or more and 1000 ppm by volume or less, which inhibits the formation of an imine for a long period of time.

In the alkylamine composition of the present disclosure, setting the oxygen content to less than 1 ppm by volume is difficult. In contrast, setting the oxygen content to higher than 1000 ppm by volume may increase the imine content even when the water content is within the above range. Use of such an alkylamine composition as a raw material in the production of pharmaceutical products and the like may allow the imine itself to possibly affect the properties of the product.

The alkylamine composition of the present disclosure preferably contains the alkylamine in an amount of 99.9% by volume or more.

The alkylamine composition of the present disclosure containing the alkylamine in an amount of 99.9% by volume or more has a high alkylamine purity and can keep an impurity content small over a long period of time. Such a composition can be more suitable for use in pharmaceutical products and the like.

A method for storing an alkylamine composition of the present disclosure includes: filling a container with the alkylamine composition; and storing the container filled with the alkylamine composition at 10° C. or higher and 45° C. or lower.

The method for storing an alkylamine composition of the present disclosure includes: filling a container with an alkylamine composition; and storing the container filled with the alkylamine composition at 10° C. or higher and 45° C. or lower. In the method, the alkylamine composition used is the alkylamine composition of the present disclosure and the temperature of the container during storage is 10° C. or higher and 45° C. or lower, which can inhibit the formation of an imine over a long period of time.

In the method for storing an alkylamine composition of the present disclosure, storage of the container filled with the alkylamine composition at a temperature of lower than 10° C. is not favorable as the cost of cooling increases. Storage of the container filled with the alkylamine composition at a temperature of higher than 45° C. is not favorable as an imine is likely to be formed.

According to the method for storing an alkylamine composition of the present disclosure, an increase in an imine compound is not more than 100 ppm by volume even after storage at 25° C. for a month. As above, the formation of an imine is inhibited even after storage for a long period of time.

In the method for storing an alkylamine composition of the present disclosure, the container is preferably made of stainless steel (SUS), manganese steel, nickel steel, or chrome molybdenum steel.

In the method for storing an alkylamine composition of the present disclosure, the container made of stainless steel (SUS), manganese steel, nickel steel, or chrome molybdenum steel has sufficient mechanical strength, which enables safe storage. In addition, since impurities hardly dissolve from the container, an increase in impurities such as an imine can be inhibited even after storage of the alkylamine composition for a long period of time.

Advantageous Effects of Invention

The alkylamine composition of the present disclosure contains a very small amount of water. Such a very small amount of water is unlikely to cause production of a product that does not meet the required properties and can inhibit, for a long period of time, the formation of an imine that is likely to cause production of a product that does not meet the required properties when the alkylamine composition is used in the production process of pharmaceutical products and the like. Even when water is considered a potentially problematic impurity, the total amount of impurities including water is small, allowing the composition to be suitable for use in pharmaceutical products and the like.

DESCRIPTION OF EMBODIMENTS

Hereinafter, the present disclosure is described in detail. The following descriptions of constituent elements are examples of embodiments of the present disclosure. The present disclosure is not limited to these specific descriptions. Various modifications can be made within the scope of the gist of the present disclosure.

The alkylamine composition of the present disclosure contains: an alkylamine represented by the following formula (1) in an amount of 99.5% by volume or more; and water in an amount of 10 ppm by mass or more and 100 ppm by mass or less:

[Chem. 2]

(1)

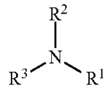

wherein N is a nitrogen atom; $R^1$ is a C1-C10 hydrocarbon group optionally having a ring, a heteroatom, or a halogen atom; $R^2$ and $R^3$ are each independently a hydrogen atom or a C1-C10 hydrocarbon group optionally having a ring, a heteroatom, or a halogen atom; provided that the hydrocarbon group, when it has a carbon number of 3 or more, may have a branched chain structure or a ring structure and that the heteroatom in the hydrocarbon group is a nitrogen atom, an oxygen atom, a sulfur atom, or a phosphorus atom; further, $R^1$ and $R^2$, when both of them are hydrocarbon groups having a carbon number of 1 or more, may be directly bonded to each other to form a ring structure;

further, $R^1$ or $R^2$, which is directly bonded by a double bond to form a ring structure, may form an aromatic ring in the absence of $R^3$; $R^1$, $R^2$, and $R^3$ may be hydrocarbon groups which are the same as or different from one another; and $R^1$ has at least one hydrogen atom at α carbon bonded to the nitrogen atom.

The alkylamine composition of the present disclosure contains water in an amount of 10 ppm by mass or more and 100 ppm by mass or less, which can inhibit the formation of an imine, which is an impurity, over a long period of time. The alkylamine composition contains water in an amount of 10 ppm by mass or more and 100 ppm by mass or less. Such a very small amount of water is unlikely to cause production of a product that does not meet the required properties when the alkylamine composition is used in the production process of pharmaceutical products and the like. The water in the composition can inhibit the formation of an imine that is likely to cause production of a product that does not meet the required properties. Even when water is considered a potentially problematic impurity, the total amount of impurities including water is small, allowing the composition to be suitable for use in pharmaceutical products and the like.

In the alkylamine represented by the formula (1), examples of the halogen atom optionally contained in the hydrocarbon group include fluorine, chlorine, bromine, and iodine atoms. The hydrocarbon group, when it has a carbon number of 3 or more, may be a hydrocarbon group with a branched chain such as an isopropyl group, an aromatic hydrocarbon group such as a phenyl group, or an alicyclic hydrocarbon group containing no conjugated double bond other than an aromatic conjugated double bond, such as a cyclohexyl group. The alkylamine represented by the formula (1) may also be a heterocyclic amine having a five-membered or six-membered ring structure.

Examples of the alkylamine include: tertiary amines such as trimethylamine, triethylamine, dimethylethylamine, and diethylmethylamine; secondary amines such as dimethylamine, diethylamine, di-n-propylamine, diisopropylamine, dibutylamine, N-methylethylamine, N-methylpropylamine, N-methylbutylamine, and N-methylpentylamine; heterocyclic amines such as pyrrolidine, piperidine, piperazine, pyridine, and pyrazine; and primary amines such as methylamine, ethylamine, n-propylamine, isopropylamine, n-butylamine, sec-butylamine, isobutylamine, n-pentylamine, n-hexylamine, and n-heptylamine.

In the formula (1), $R^2$ and $R^3$ are preferably hydrogen atoms. In the formula (1), $R^1$ is preferably a hydrocarbon group having no heteroatom or halogen atom.

In the formula (1), $R^1$ is a C1-C10 hydrocarbon group, preferably a C1-C7 hydrocarbon group, more preferably a C3-C6 hydrocarbon group.

The alkylamine is therefore preferably n-propylamine, isopropylamine, n-butylamine, sec-butylamine, or isobutylamine, particularly preferably n-butylamine.

When the alkylamine composition is a n-butylamine composition, the content of alkylamines other than n-butylamine, such as isobutylamine, is preferably 0.05% by volume or less. When the content of alkylamines other than n-butylamine is high, a product that does not meet the required properties may possibly be produced in the production process of pharmaceutical products and the like.

The alkylamine composition of the present disclosure is a high purity alkylamine composition containing 99.5% by volume or more of the alkylamine represented by the formula (1). The alkylamine composition of the present disclosure preferably contains the alkylamine in an amount of 99.9% by volume or more, particularly preferably 99.95% by volume or more. With higher purity, the alkylamine composition is more suitable for use in the production process of pharmaceutical products and the production process of semiconductor devices.

The alkylamine composition of the present disclosure contains water in an amount of 10 ppm by mass or more and 100 ppm by mass or less, preferably in an amount of 30 ppm by mass or more and 80 ppm by mass or less. This is because the formation of an imine can be further inhibited. An alkylamine purified by distillation or the like may only contain water in an amount of less than 10 ppm in some cases. In such cases, water such as ultrapure water is added to adjust the water content. Before the addition, the dissolved oxygen in the water to be added is preferably removed by nitrogen bubbling or the like.

The alkylamine composition of the present disclosure may contain oxygen in an amount of 1 ppm by volume or more and 1000 ppm by volume or less, or in an amount of 10 ppm by volume or more and 100 ppm by volume or less.

An alkylamine tends to form an imine during long-term storage, and forms water at the same time. Since an imine formed during storage of an alkylamine composition is a compound having a carbon-nitrogen double bond (C═N) and water ($H_2O$) is formed at the same time, oxygen and an amine contained in the alkylamine composition presumably react with each other to form an imine. Therefore, an alkylamine composition containing less oxygen is presumably less likely to suffer the formation of an imine. However, reducing the oxygen content to less than 1 ppm by volume is not easy. The formation of an imine in an alklylamine composition containing oxygen in an amount of 1000 ppm by volume or less can be surely inhibited by setting the water content of the alkylamine composition to 10 ppm by mass or more and 100 ppm by mass or less.

The alkylamine composition may contain other impurities in addition to the alkylamine, water, and oxygen. Examples of the other impurities include inert gas and nitrogen. The total content of these impurities is preferably 20 ppm by volume or less.

Next, a method for storing the alkylamine composition is described.

The method for storing an alkylamine composition of the present disclosure includes: filling a container with the alkylamine composition of the present disclosure; and storing the container filled with the alkylamine composition at 10° C. or higher and 45° C. or lower.

In the method for storing an alkylamine composition of the present disclosure, the filling includes filling a container with the alkylamine composition.

In this operation, the container is preferably filled with the composition in a liquid state. The alkylamine composition of the present disclosure is liquid at the above temperatures in most cases, and therefore can be used in a liquid state in filling a storage container. Even when the alkylamine composition of the present disclosure is gaseous at room temperature, it can be liquefied by filling under pressure. In this case, the vapor pressure is not very high, which enables safe filling of a metal container normally used for cylinders or the like with the composition using a pump or the like.

Containers to be filled with the alkylamine composition are not limited. Examples thereof include containers made of stainless steel (SUS), manganese steel, nickel steel, and chrome molybdenum steel.

When storing the alkylamine composition after filling the container, the container filled with the alkylamine composition is stored at 10° C. or higher and 45° C. or lower.

Storage at a temperature of lower than 10° C. is not favorable as it requires cooling of the storage container to lower than 10° C., which unfavorably increases the cost of storage. Storage at a temperature of higher than 45° C. is not favorable as it requires heating, which is costly for heating and allows easy formation of an imine.

In the storing, the container filled with the alkylamine composition should be stored in a storage unit that can be kept at around room temperature. Preferably, the container is stored in a storage unit that can be kept at a constant temperature of around 25° C.

In the alkylamine composition of the present disclosure, an increase in an imine compound is not more than 100 ppm by volume even after storage at 25° C. for a month. Therefore, according to the method for storing an alkylamine composition of the present disclosure, the formation of an imine can be sufficiently inhibited even during long-term storage.

After storage of the alkylamine composition at 25° C. for a month, the increase in an imine compound is preferably not more than 80 ppm by volume, more preferably not more than 30 ppm by volume.

When the alkylamine composition is actually used after storage of the container filled with the alkylamine composition for a predetermined period of time, the container containing the alkylamine composition is transferred to the site, and the container is heated to the boiling point of the alkylamine composition or a temperature close to the boiling point. Thus, the alkylamine composition is vaporized into a gas composition to be supplied to the intended equipment via a pipe or the like. Alternatively, the alkylamine composition of the present disclosure after storage can be taken out in a liquid state and supplied to the intended equipment via a pipe or the like.

In the case where the storage location and the production equipment and the like are close to each other, providing piping connecting the storage container with the production equipment and the like enables appropriate supply of the alkylamine composition of the present disclosure to the production equipment and the like.

Examples of methods for heating the container include covering the container with a mantle heater and covering the container with a jacket in which a heat medium such as hot water or steam is circulated.

The flow rate of the gas composition depends on the configuration of the intended equipment and is not limited. The flow rate of the gas composition can be controlled by a mass flow controller, for example.

EXAMPLES

The following is an example of a more specific disclosure of an embodiment of the present disclosure. The present disclosure is not limited to these examples only.

Example 1

A raw material containing n-butylamine was distilled to obtain a n-butylamine composition with a purity of 99.99% by volume and a water content of 8 ppm by mass. The oxygen concentration was considered to be 1 ppm by volume or more and 1000 ppm by volume or less. The oxygen concentration can be converted from the imine compound content by liquid-phase analysis using a gas chromatograph analyzer (GC-2030, available from Shimadzu Corporation, Detector: FID). Specifically, the oxygen concentration can be calculated from the estimated mechanism that 2 mol of butylamine and 1 mol of $O_2$ generate 1 mol of an imine compound.

Ultrapure water was then added to the n-butylamine composition, thereby preparing a n-butylamine composition with a water content of 50 ppm by mass. Since the amount of dissolved oxygen in ultrapure water was negligibly small, the oxygen concentration of the n-butylamine composition was almost the same in each example.

A 1-L SUS container was filled with 0.9 L of the n-butylamine composition obtained from the preparation at room temperature and stored at 25° C.

Then, the n-butylamine composition in the container was sampled every month for measurement of the purity of n-butylamine and the imine compound (N-butylbutanimine) content by gas chromatography using a gas chromatograph analyzer (GC-2030, available from Shimadzu Corporation, detector: FID). The water content was measured using a Karl Fischer moisture titrator (instrument: Kyoto Electronics Manufacturing Co., Ltd., MKC-610). Table 1 shows the results.

TABLE 1

| | Purity of n-butylamine (vol %) | Water content (mass ppm) | N-Butylbutanimine content (volume ppm) |
|---|---|---|---|
| Before test | 99.99 | 50 | 0 |
| After one month | 99.99 | 51 | 10 |
| After two months | 99.99 | 52 | 12 |
| After three months | 99.99 | 54 | 14 |

Example 2

An n-butylamine composition was obtained as in Example 1, except that ultrapure water was added to set the water content of the n-butylamine composition to 90 ppm by mass. A container was filled with the obtained n-butylamine composition at room temperature and stored at 25° C. Then, the purity of n-butylamine and the imine compound (N-butylbutanimine) content of the n-butylamine composition were measured by gas chromatography every month. Similarly, the water content was measured with a Karl Fischer moisture titrator every month. Table 2 shows the results.

TABLE 2

| | Purity of n-butylamine (vol %) | Water content (mass ppm) | N-Butylbutanimine content (volume ppm) |
|---|---|---|---|
| Before test | 99.99 | 90 | 0 |
| After one month | 99.99 | 90 | 0 |
| After two months | 99.99 | 91 | 5 |
| After three months | 99.99 | 91 | 5 |

Comparative Example 1

An n-butylamine composition was obtained as in Example 1, except that ultrapure water was not added after distilling a raw material containing n-butylamine to obtain n-butylamine with a purity of 99.99% by volume and a water content of 8 ppm by mass. A 1-L SUS container was filled with 0.9 L of the obtained n-butylamine composition and stored at 25° C.

Then, the purity of n-butylamine and the imine compound (N-butylbutanimine) content of the n-butylamine composition were measured by gas chromatography every month. Similarly, the water content was measured with a Karl Fischer moisture titrator every month. Table 3 shows the results.

TABLE 3

| | Purity of n-butylamine (vol %) | Water content (mass ppm) | N-Butylbutanimine content (volume ppm) |
|---|---|---|---|
| Before test | 99.99 | 8 | 0 |
| After one month | 99.98 | 20 | 130 |
| After two months | 99.98 | 24 | 141 |
| After three months | 99.98 | 27 | 146 |

As is clear from the results shown in Tables 1 to 3, in Comparative Example 1 in which the water content was less than 10 ppm by mass, the amount of the imine compound increased significantly with time, accompanied by a slight increase in water content. In contrast, in Examples 1 and 2 in which the water content was 10 ppm by mass or more, the amount of the imine compound did not increase so much. Considering the sum of the amount of water and the amount of the imine compound as the total amount of impurities, the concentration of impurities was lower in Examples 1 and 2 than in Comparative Example 1, because daring addition of water inhibited the formation of the imine compound.

The present application claims priority to Japanese Patent application No. 2020-115757 filed on Jul. 3, 2020 under the Paris Convention and provisions of national law in a designated State. The disclosure of the application is hereby incorporated by reference in its entirety.

The invention claimed is:

1. An alkylamine composition comprising:

an alkylamine, which is n-butylamine and in an amount of 99.5% by volume or more; and water in an amount of 30 ppm by mass or more and 100 ppm by mass or less.

2. The alkylamine composition according to claim 1, further comprising oxygen in an amount of 1 ppm by volume or more and 1000 ppm by volume or less.

3. The alkylamine composition according to claim 1, wherein the alkylamine composition contains the alkylamine in an amount of 99.9% by volume or more.

4. A method for storing an alkylamine composition, comprising:

filling a container with an alkylamine composition; and storing the container filled with the alkylamine composition at 10° C. or higher and 45° C. or lower, wherein the alkylamine composition comprises:

an alkylamine, which is n-butylamine and in an amount of 99.5% by volume or more; and water in an amount of 30 ppm by mass or more and 100 ppm by mass or less.

5. The method for storing an alkylamine composition according to claim 4, wherein an increase in an imine compound is not more than 100 ppm by volume even after storage at 25° C. for a month in the storing.

6. The method for storing an alkylamine composition according to claim 4, wherein the container is made of stainless steel, manganese steel, nickel steel, or chrome molybdenum steel.

7. The method for storing an alkylamine composition according to claim 4, wherein the alkylamine composition further comprises oxygen in an amount of 1 ppm by volume or more and 1000 ppm by volume or less.

8. The method for storing an alkylamine composition according to claim 4, comprising storing the container filled with the alkylamine composition for more than one month.

9. The method for storing an alkylamine composition according to claim 4, wherein after storing the container filled with the alkylamine composition at 25° C. for one month, the alkylamine composition comprises the alkylamine in the amount of is 99.99% by volume or more.

10. The method for storing an alkylamine composition according to claim 4, wherein the alkylamine composition comprises the water in the amount of 50 ppm by mass or more and 100 ppm by mass or less.

* * * * *